US00PP09736P

United States Patent [19]

Carmi

[11] Patent Number: Plant 9,736

[45] Date of Patent: Dec. 10, 1996

[54] HYBRID TEA ROSE PLANT NAMED 'LIGHT CAROLA'

[75] Inventor: Carmel Carmi, Moshav Hayogev, Israel

[73] Assignee: Yoval Agricultural Products Ltd., Israel

[21] Appl. No.: 323,076

[22] Filed: Oct. 14, 1994

[51] Int. Cl.[6] ..... A01H 5/00

[52] U.S. Cl. ..... Plt./20

[58] Field of Search ..... Plt./11, 20, 21

[56] References Cited

U.S. PATENT DOCUMENTS

P.P. 4,391 3/1979 Delbard ..... Plt./20

P.P. 8,290 7/1993 Carmel ..... Plt./20

P.P. 8,620 3/1994 Carmel ..... Plt./20

*Primary Examiner*—Howard J. Locker

*Attorney, Agent, or Firm*—Pollock, Vande Sande & Priddy

[57] ABSTRACT

A new and distinct rose plant of the hybrid tea class named 'Light Carola'. The plant is characterized by vigorous growth, non-fragrant flowers with red (RHS 47 A - 57 B) petals, early and prolific flower production, and fast and good propagating features.

3 Drawing Sheets

CROSS REFERENCE TO RELATED PATENTS

The new and distinct cultivar described and illustrated herein is related to the cultivar 'Carola', the subject of U.S. Plant Pat. No. 8,290, issued Jul. 6, 1993, which in turn is a mutation of 'Deladel' ('Mme. G. Delbard'), the subject of U.S. Plant Pat. No. 4,391, issued Mar. 6, 1979.

FIELD OF THE INVENTION

The present invention is concerned with a new variety of a Hybrid Tea rose discovered by me and being a mutation of 'Carola', U.S. Plant Pat. No. 8,290, issued Jul. 6, 1993.

BACKGROUND OF THE INVENTION

This mutation was discovered as a branch on a 'Carola' plant in 1993 on a cultivated area in a farm, located in Moshav Ha'yogev, located in Izra'el Valley, Israel, with an average night temperature of 25° C. in summer and 0°–5° C. in winter.

The branch was vegetatively propagated from cuttings by self-rooting. From these cuttings plants were grown in a greenhouse where they were further vegetatively propagated from cuttings by self-rooting.

The resulting plants were found to be stable in their botanical characteristics, as are described below and as illustrated by typical plants parts in the attached photographs.

Asexual propagation of this new variety was performed at Moshav Ha'yogev, Israel.

The presently claimed cultivar was a natural mutation of the cultivar 'Carola'.

All color definitions in this application are taken from The Royal Horticultural Society of London, England (R.H.S.), Colour Chart.

The data in the following table of comparison is based on observations made in the greenhouse at Moshav Ha'yogev, where plants were grown side-by-side, under the same conditions and under the same roof. The following observations were made between the present invention and the parent plant.

| Prickle(s): | 'CAROLA' | 'LIGHT CAROLA' |
|---|---|---|
| shape: upper side | concave to straight | straight |
| Leaf: | | |
| size (mm): | | |
| length | 140–170 | 140–160 |
| width | 110–150 | 100–130 |
| Petiole: | | |
| length (mm) | ca. 20 | 20–25 |
| Foliage: | | |
| young: color of upper side | RHS 144B yellow-green | RHS 141B light green |
| mature: color of lower side | red-green | green |
| Flowering stem: | | |
| length (cm) | 70–80 | 60–80 |
| color | medium green | green |
| Flower: | | |
| diameter (mm) | ca. 110 | ca. 100 |
| number of petals | 33–40 | 28–39 |
| Sepal: | | |
| length (mm) | 40–55 | 35–48 |
| Petal: | | |
| size (mm): | | |
| length | 50–60 | 40–60 |
| width | 55–65 | 40–50 |
| color of upper side | RHS 53A dark red | RHS 47A/57B red |
| color of basal spot | RHS 155D white | RHS 155A white |
| color of lower side | RHS 53C dark red | RHS 52A red |

SUMMARY OF THE INVENTION

The present invention provides a Hybrid Tea rose variety which includes the following characteristics which distinguish the new variety from the cultivar 'Carola', to which it is related, and for which the following differences have been noted:

Distinctly different in the following:

Prickles: Shape of upper side.
Leaf: Size.
Petiole: Length.
Foliage: Color.
Flower: Diameter, number of petals.
Sepal: Length.
Petal: Size, color, color of basal spot.

The relationship of the presently claimed cultivar to other related cultivars as follows:

'Deladel' --> 'Carola' --> 'Odem' --> 'Seemore' -->
'Carola' --> 'Light Carola'

The following table of comparison present the differences between the cultivars in the family:

| U.S. Plant Patent/ Application | 'DELADEL' 4,391 | 'CAROLA' 8,290 | 'ODEM' 8,620 | 'LIGHT CAROLA' 08/ 323,076 | 'SEEMORE' 08/ 322,487 |
|---|---|---|---|---|---|
| Plant: | | | | | |
| growth habit | upright | upright | semi-upright | upright | semi-upright |
| Stem: | | | | | |
| color: mature | green-brown, corky | corky | green-brown corky | green-brown, | green-brown |
| Young shoot: anthocyanin coloration | | strong | medium to strong | strong | medium to strong |
| hue of anthocyanin coloration | no data | red-brown | purple | red-brown | red-brown |
| Prickle (s): | | | | | |
| size: | | | | | |
| length (mm) | no data | 5 | 5 | 4.5 | 5 |
| height (mm) | no data | 6 | 6 | 5.5 | 6 |
| shape: upper side short prickles: | long base hooked downward | concave to straight | concave | straight | concave to straight |
| quantity per 10 cm at center of stem long prickles: | many | 58 | none | 59 | none |
| quantity per 10 cm at center of stem | many | 8 | 7 | 9 | 8 |

-continued

| U.S. Plant Patent/ Application | 'DELADEL' 4,391 | 'CAROLA' 8,290 | 'ODEM' 8,620 | 'LIGHT CAROLA' 08/ 323,076 | 'SEEMORE' 08/ 322,487 |
|---|---|---|---|---|---|
| Leaf: | | | | | |
| size: | | | | | |
| length (mm) | no data | 140–170 | 120–150 | 140–160 | 120–150 |
| width (mm) | no data | 110–150 | 75–115 | 100–130 | 75–115 |
| green color | no data | medium to dark | medium | medium to dark | medium |
| glossiness of upper side | no data | absent to very weak | weak | absent to very weak | weak |
| Leaflet: | | | | | |
| cross section | oval pointed often curved with convex upper surface | slightly convex | straight | slightly convex | straight |
| undulation of margin | no data | absent to very weak | weak to medium | absent to very weak | weak to medium |
| Terminal leaflet: | | | | | |
| width: (mm) | no data | ca. 35 | 30–43 | ca. 33–38 | 30–43 |
| blade: length (mm) | no data | ca. 60 | 50–65 | ca. 60 | 50–65 |
| Petiole: | | | | | |
| length (mm) | color: green | ca. 20 | 15–20 | ca. 20–25 | 15–20 |
| rachis | | hairy | smooth | smooth | hairy |
| Foliage: | | | | | |
| young: color of upper side (RHS) | light brown | 144B yellow-green | 145B yellow-green | 141B light green | 141B light green |
| mature: color of lower side | green | red-green | red-green | green | green |
| Flowering stem: | | | | | |
| length (cm) | 70–90 | 70–80 | 40–60 | 60–80 | 40–70 |
| color | no data | medium green | green | green | light green |
| Flower pedicel: | | | | | |
| number of hairs or prickles | no data | few | very few to few | few | very few to few |
| Flower bud: | | | | | |
| longitudinal section | pointed ovoid | circular | ovoid | circular | ovoid |
| Flower: | | | | | |
| diameter (mm) | average 102–114 | ca. 110 | ca. 80 | ca. 100 | ca. 80 |

-continued

| U.S. Plant Patent/ Application | 'DELA-DEL' 4,391 | 'CARO-LA' 8,290 | 'ODEM' 8,620 | 'LIGHT CARO-LA' 08/ 323,076 | 'SEE-MORE' 08/ 322,487 |
|---|---|---|---|---|---|
| size of bloom | no data | large | medium | large | medium |
| height (mm) | no data | 50–70 | 30–50 | 50–70 | 30–50 |
| fading with age | none to end of third day | none | slight fading begins after 7–10 days | none | fading begins after 7–10 days |
| view from above | rounded | rounded to star shaped | rounded | rounded to star shaped | rounded |
| number of petals | 30–35 | 33–40 | 40–43 | 28–39 | 43–58 |
| life (days): on the plant | no data | 20–30 | 15–20 | 20–30 | 17–21 |
| in a vase | no data | 12–15 | 15–18 | 12–15 | 12–15 |
| Sepal: | | | | | |
| length (mm) | no data | 40–55 | 30–43 | 35–48 | 30–43 |
| extensions | slight | strong | medium | strong | medium |
| Petal: | | | | | |
| size: | | | | | |
| length (mm) | no data | 50–60 | 37–45 | 40–60 | 37–45 |
| width (mm) | no data | 55–65 | 39–49 | 40–50 | 39–49 |
| upper side: color | Blood red | RHS 53A dark red | RHS 46AB dark red Currant red | RHS 47A/57B red | RHS 57A/58B purple red |
| basal spot at base of petal: size | very small | medium | small | medium | small |
| color | yellow | RHS 155C white | RHS 3B yellow | RHS 155A white | RHS 3B yellow |
| lower side: color | Blood red | RHS 53C dark red | RHS 52A deep red Crimson | RHS 52A red | RHS 55D whitish-purple, very light purple |
| reflexing of margin | strong | strong | medium | strong | medium |
| undulation of margin | no data | weak | very weak to weak | weak | very weak to weak |
| Stamen: predominant color of filament | yellow | purple | orange-red | purple | yellow-orange |
| Style: | | | | | |
| hairiness of upper half | no data | medium | absent | medium | absent |
| Stigma: | | | | | |
| position as compared with anthers | no data | above | same level | above | above |
| color | Amber yellow | RHS 4C light yellow | RHS 155C white | RHS 4C light yellow | RHS 4D light yellow |

-continued

| U.S. Plant Patent/ Application | 'DELA-DEL' 4,391 | 'CARO-LA' 8,290 | 'ODEM' 8,620 | 'LIGHT CARO-LA' 08/ 323,076 | 'SEE-MORE' 08/ 322,487 |
|---|---|---|---|---|---|
| Seed Vessel: | | | | | |
| size: | no data | medium | small | medium | small |
| length (mm) | no data | 11 | 8 | 11 | 8 |
| diameter (mm) | no data | 12 | 11 | 12 | 7 |
| shape of longitudinal section | no data | pitcher shaped | funnel shaped | pitcher shaped | funnel shaped |
| Anthers: | | | | | |
| color | yellow | red | yellow | red | light yellow |
| Filament: | | | | | |
| color | yellow-red | yellow-red | pink margin: orange | yellow-red | yellow |

BRIEF DESCRIPTION OF THE DRAWINGS

Sheet 1 represents a typical specimen of the present invention, illustrating a flower bud at picking stage, a part of the stem, leaflets, and flowers at various opening stages;

Sheet 2 represents a side-by-side comparison of the flower size, bud size and color of petal between a typical specimen of the present invention, 'Light Carola' (on the left) and the parent variety, 'Carola' (on the right); and Sheet 3 represents another side-by-side comparison of various flower parts between a typical specimen of the present invention, 'Light Carola' (on the left) and the parent variety, 'Carola' (on the right).

The colors in the drawings are as true as is reasonably possible in an illustration, depicting green and red colors. The plants illustrated in Sheets 2 and 3 were grown under exactly the same conditions, in a greenhouse at Moshav Ha'yogev, each on its own roots, and being visibly healthy.

BOTANICAL DESCRIPTION

The following observations were made in Moshav Ha'yogev Israel in 1993 in a greenhouse:

Plant:

*Form.*—Bush.

*Growth habit.*—Upright.

*Height (cm).*—150–200.

*Spread (cm).*—Ca. 80.

Wood:

*Color.*—Mature, Light brown.

*Bark.*—Color: young, Green.

Mature, Light brown.

Stem:

*Color.*—Young, R.H.S. 143 B/152 B, green-yellow green. Mature, RHS 143 A green.

Young shoot:

*Anthocyanin coloration.*—Strong.

*Hue of anthocyanin coloration.*—Red-brown.

Prickle(s): Present.
*Size.*—Length (mm): ca. 4.5. Height (mm): ca. 5.5.
*Shape.*—Upper side: straight. Lower side: concave.
*Color.*—Young: Bases: R.H.S. 173 B grey orange. upper part: R.H.S. 144 B yellow green. Mature: bases: R.H.S. 173 A/176 grey orange. upper part: R.H.S. 152 BC yellow green.
Short prickles:
*Quantity.*—Many.
*Number per* 10 *cm at center of stem.*—Many (59).
Long prickles:
*Number per* 10 *cm at center of stem.*—Few (9).
Leaf:
*Size.*—Length (mm): 140–160. Width (mm): 100–130.
*Green color.*—Medium to dark.
*Glossiness of upper side.*—Absent to very weak.
*Number of leaflets in the compound leaf.*—3, 5, or 7.
Leaflet:
*Cross section.*—Slightly convex.
*Undulation of margin.*—Absent to very weak.
*Margin.*—Serrated.
Terminal leaflet:
*Length of blade* (*mm*).—Ca. 60.
*Maximum width* (*mm*).—Ca. 33–38.
*Shape of base.*—Rounded.
Petiole:
*Length* (*mm*).—Ca. 20–25.
*Rachis.*—Straight, flat, smooth.
*Color.*—R.H.S. 144 A, yellow green.
Foliage:
*Color.*—Young: upper side: R.H.S. 165 A, grey orange. Lower side: R.H.S. 178 A/183 B, grey-red purple. Mature: upper side: R.H.S. 137 A/147 A, green-yellow green. Lower side: R.H.S. 137 C/147 B, green-yellow green.
Stipule: Stitched, split tip.
Bloom:
*Borne.*—Multiply/in a Cluster.
Flowering shoot:
*Number of flowers* (*after the other flower buds are pinched off*).—Few (3–5).
Flowering habit: Continuous.
Flowering stem:
*Length* (mm).—Ca. 60–80.
*Color.*—Green.
Flower pedicel:
*Number of hairs or prickles.*—Few.
Flower bud:
*Longitudinal section.*—Circular.
*Size.*—Large (50–70 mm).
Flower:
*Type.*—Double.
*Diameter.*—Ca. 100 mm.
*Fragrance.*—None.
*View from above.*—Rounded to starshaped.
*Side view.*—Upper side: Flattened-convex. Lower side: flat.
*Number of petals.*—28–39.
*Life.*—on the plant: 20–23 days. In a vase: 12–15 days.
Fading with age.—None.
Petal:
*Size.*—Length(mm): ca. 60–40.
*Width* (*mm*): ca. 40–50.
*Shape.*—Rounded.
*Color.—upper side.*—Middle zone: R.H.S. 47A/57B red. Marginal zone: R.H.S. 47A/57B red. Basal spot: present. Basal spot: size: medium. color: R.H.S. 155A white.
*Color.—lower side.*—Middle zone: R.H.S. 52A red. Marginal zone: R.H.S. 52A red. Basal spot: present. Basal spot: color: white.
*Reflexing of margin.*—Strong.
*Undulation of margin.*—Weak.
Sepal:
*Color.*—Upper side: R.H.S. 144 AB, yellow green. Lower side: R.H.S. 144 A, yellow green.
*Length* (*mm*).—Ca. 35–48.
*Extensions.*—Strong.
*Color.*—Upper side: green-yellow, white hairs. Lower side: green-yellow.
Stamen:
*Predominant color of filament.*—Purple.
Style:
*Length.*—Long.
*Predominant color.*—Purple.
*Hairiness of upper half.*—Medium.
Stigma:
*Position as compared wtih anthers.*—Above.
*Color.*—R.H.S. 4C light yellow.
Seed vessel:
*Size.*—medium.
*Length* (*mm*).—Ca. 11.
*Diameter* (*mm*).—Ca. 12.
*Shape of longitudinal section.*—Pitcher shaped.
*Color.*—White-yellow.
*Description.*—Long, hairy.
Pollen:
*Color.*—Red-yellow.
Anthers:
*Color.*—Red.
*Quantity.*—Many.
*Arrangement.*—Peripheral.
Filament:
*Color.*—Yellow-red.
Time from planting to beginning of flowering: Approx. 4 months.
Self-rooting: Very good.

The cultivar is intended as and is suitable as a greenhouse rose. The cultivar bears blooms multiply. Blooms may be borne in a cluster.

When reference is made herein to "Number of flowers few," it is understood that such refers to 3, 4 or 5 flowers per cluster (i.e., the flowers that are left on the flowering shoot after the other flowers were pruned off). In addition, the term "fast" represents: within one month from insertion (of the cutting into the bedding) to a commercial plant. The term "good" represents: about 60–70% success in propagation.

I claim:

1. A new and distinct rose plant of the hybrid tea class named 'Light Carola' as shown and described; said plant being characterized by vigorous growth, non-fragrant flowers with red (R.H.S. 47 A-57 B) petals, early and prolific flower production, and fast and good propagating features.

* * * * *

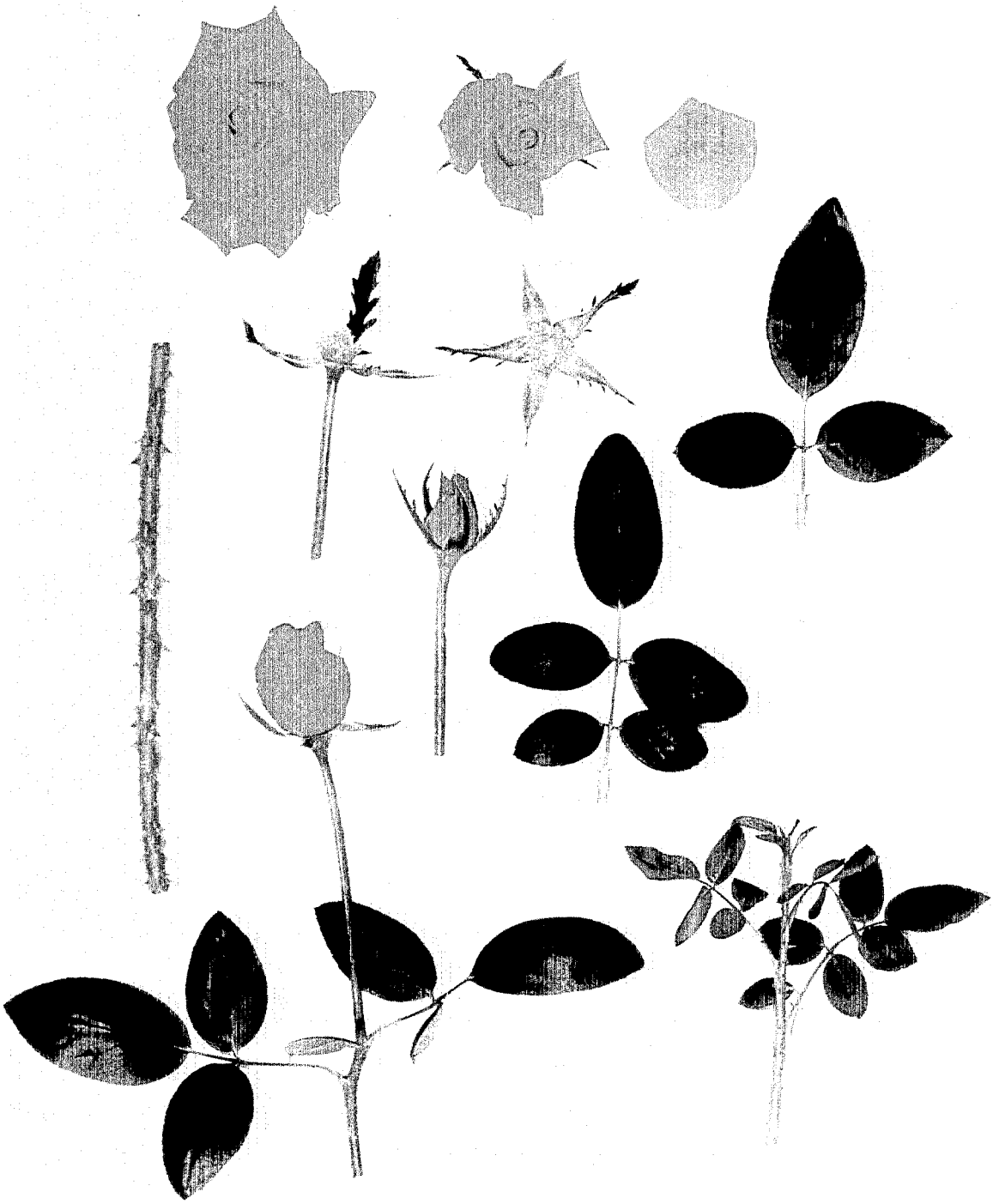

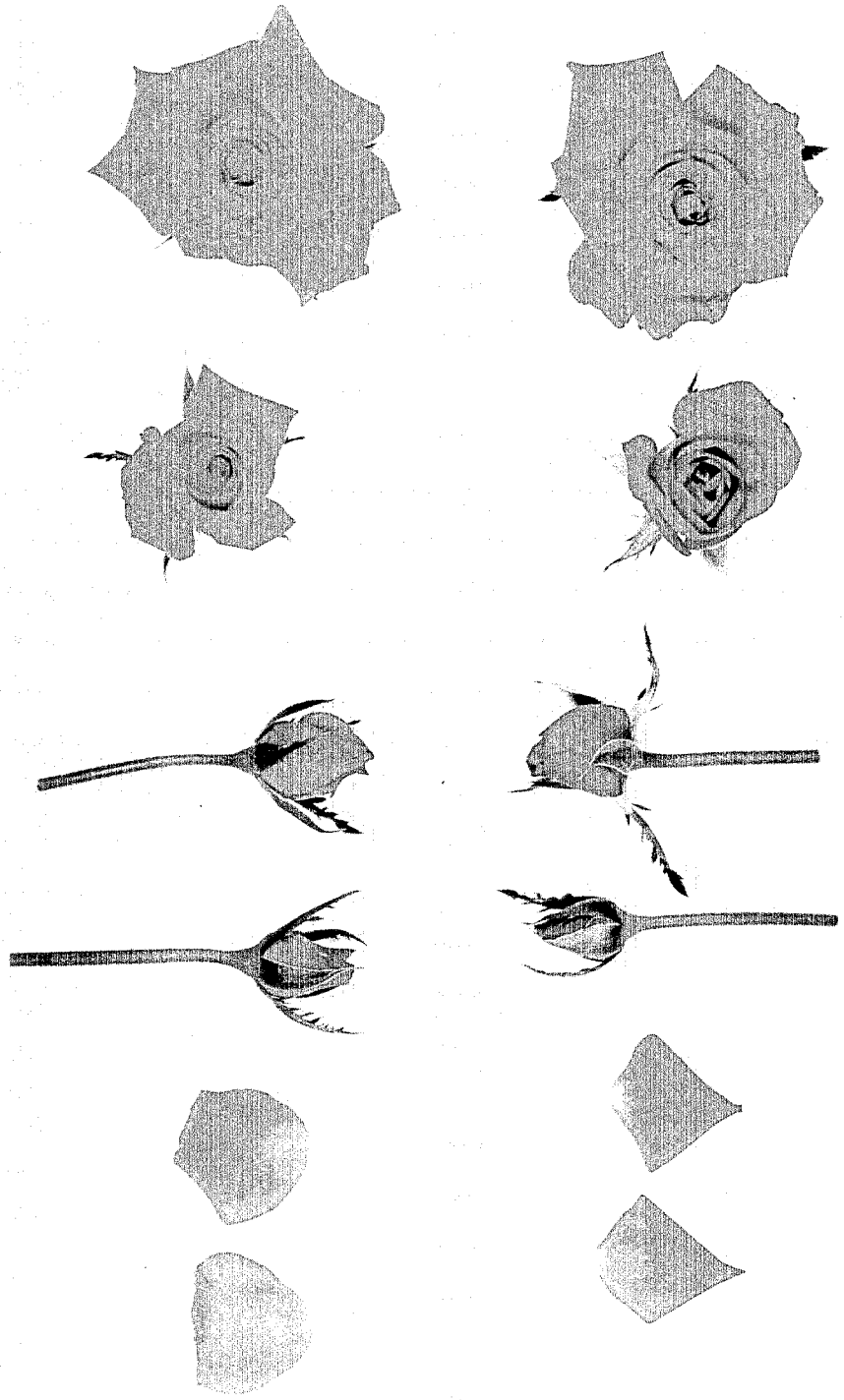

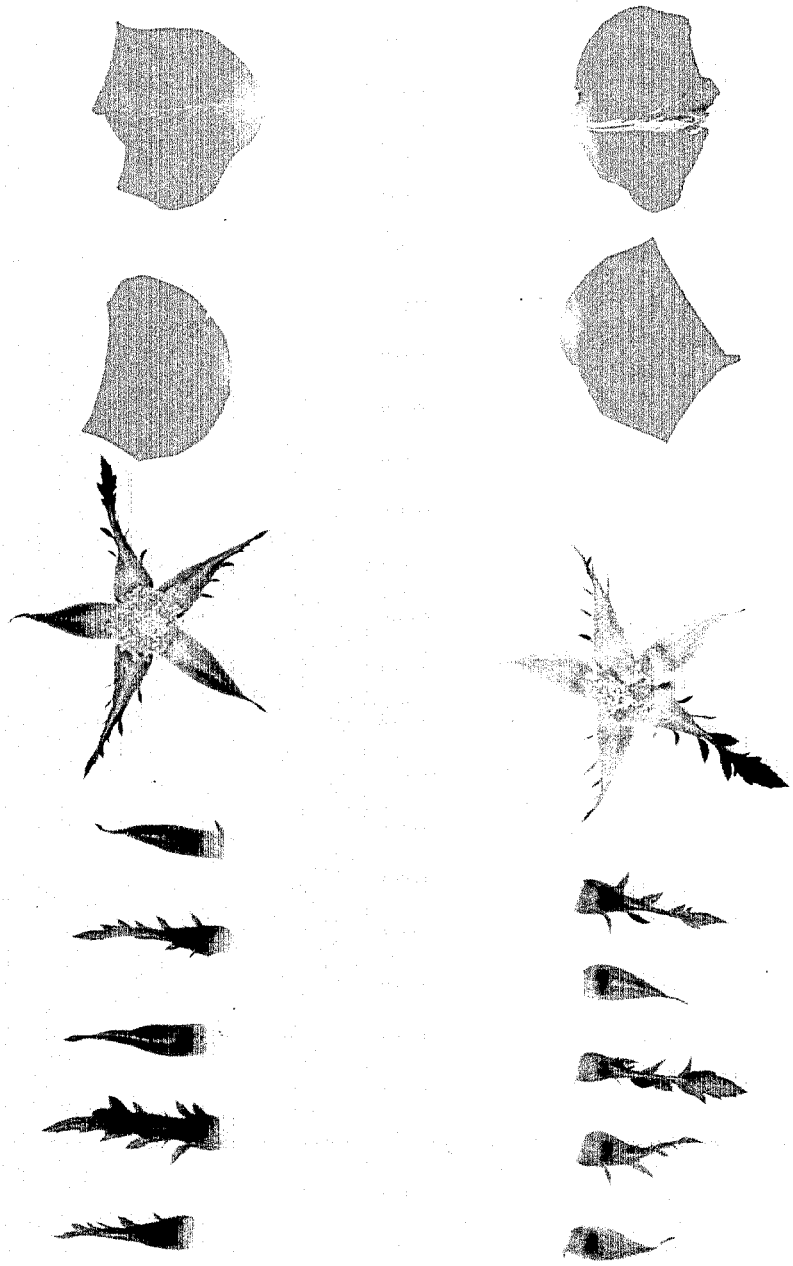
LIGHT CAROLA 3